(12) United States Patent
Kopp

(10) Patent No.: US 6,774,929 B1
(45) Date of Patent: Aug. 10, 2004

(54) SHIELDED VIDEO PROJECTION SYSTEM FOR MRI

(75) Inventor: Keith A. Kopp, Jensen Beach, FL (US)

(73) Assignee: Avotec Inc., Stuart, FL (US)

( * ) Notice: Subject to any disclaimer, the term of this patent is extended or adjusted under 35 U.S.C. 154(b) by 670 days.

(21) Appl. No.: 09/706,523

(22) Filed: Nov. 3, 2000

(51) Int. Cl.[7] .......................... H04N 9/47; G03B 21/56; G09G 5/00
(52) U.S. Cl. .............................. 348/61; 359/443; 345/8
(58) Field of Search ...................... 348/61, 359, 77–78, 348/65, 85; 324/309; 600/418; 359/443, 872

(56) References Cited

U.S. PATENT DOCUMENTS 4,901,141 A    2/1990  Costello
5,134,373 A  *  7/1992  Tsuruno et al. ............. 324/309
5,412,419 A  *  5/1995  Ziarati ........................ 348/61
5,627,902 A  *  5/1997  Ziarati ........................ 381/385
5,864,331 A  *  1/1999  Anand et al. ............... 345/656
5,877,732 A  *  3/1999  Ziarati ........................... 345/8

* cited by examiner

Primary Examiner—Gims Philippe
(74) Attorney, Agent, or Firm—McHale & Slavin, P.A.

(57) ABSTRACT

The MRI video system is a display system that provides visual stimuli to a patient who is undergoing diagnostic treatment within a magnetic resonance imagery (MRI) apparatus. The system utilizes a magnetically inert and RF shielded projector located in the close proximity to the MRI to transpose a video picture on a translucent screen inside the bore of the MRI. The patient views the screen through a prism.

11 Claims, 4 Drawing Sheets

SHIELDED VIDEO PROJECTION SYSTEM FOR MRI

FIELD OF THE INVENTION

This invention relates generally to those products used to provide visual stimuli for testing and to comfort patients undergoing diagnostic treatment and, more particularly, to a video projection system for use by operators and patients during analysis within a magnetic resonance imaging (MRI) or a magnetoencephalography (MEG) apparatus.

BACKGROUND INFORMATION

The diagnostic device known as magnetic resonance imaging (MRI) has become an invaluable tool for imaging and exploring the internal body without surgery. MRI has the ability to distinguish healthy and diseased tissue, fat and muscle, and between adjacent structures within the body which other modalities cannot demonstrate. MRI utilizes safe radio waves and a magnetic field to generate the images processed by a computer.

In operation, a typical MRI apparatus relies upon hydrogen protons which have a dipole movement and therefore behave as would a magnetic compass. In MRI scanning, the MRI apparatus operates as a large magnet wherein the protons align with the strong magnetic field but are easily disturbed by a brief radio frequency pulse of very low energy so as to alter their alignment. As the protons return to their orientation with the magnetic field, they release energy of a radio frequency that is strongly influenced by the biochemical environment. The released energy as detected and mathematically analyzed for display as a two dimensional proton density image according to the signal intensity of each tissue.

The magnetic coils of the MRI apparatus are permanently fixed within a large structure so as to form a large magnet with a very confining entrance known as the bore. A patient is placed upon a scanner table that is integrated with the MRI apparatus and slid into the middle of the bore. The problem with the bore is the extremely small area for placement of the patient and this leads to anxiety. The large and ominous appearance of the scanner together with harsh low monotone sounds which include both soft and loud thumping, produces an eerie and unnatural experience for the patient. Any patient who exhibits claustrophobic tendencies could require sedation before entering the bore. If the patient is above average in size, the problem is exasperated.

It is well known that familiarity of surroundings reduces anxiety. The introduction of familiar images to a person placed within a confining area, such as the MRI bore, will reduce if not eliminate anxiety and certain claustrophobic tendencies of various patients. This reduction can eliminate the need for medicating the patient or the need for a-restraining device, all of which may have an adverse effect on a diagnostic test. Thus, a patient who is able to listen to a family member, soft music, or watch a familiar television program will have sufficient distractions so as to avoid concentrating of the immediate surroundings which lead to increased anxiety.

In some instances, the diagnostic procedure performed with the MRI is used to evaluate a patient's response to specific visual stimuli. The operator sends a series of images to a screen which is seen by the patient during the MRI procedure and the patient's responses are included in the MRI report.

A problem with introducing conventional audio or video signals into an MRI apparatus is that the device is based upon the use of radio frequency which will disrupt signal modulation. Further, the inner area of the bore produces a magnetic field which will draw metal items when magnetized. For this reason, the audio or video signal must be in a form that is not affected by the radio frequency and transmission by a mechanism that is not easily magnetized.

An attempt to address this problem is found in U.S. Pat. No. 4,901,141 which utilizes a fiber optic taper positioned within the bore of an MRI apparatus. A CRT produced image is delivered to the fiber optic taper through a coherent image guide. The fiber optic taper expands the end of the image guide so as to provide a larger viewing surface for the patient. The problem with the fiber optic taper is that it is stationary and the patient must be positioned in a fixed location so as to be able to see the end of the optic taper. Further, to prevent distortion the patient must be located directly beneath the isocenter of the taper. Thus, the disclosure does not address different size patients, patient positioning, or near and far sighted patients For instance, a tall person may lay with their head partially outside the bore during diagnostics of the lower body whereas a child may be well encapsulated by the bore, neither of which could properly see a fixed fiber optic taper. In addition; the use of a fixed taper will interfere with auxiliary coils, such as head and c-spine coils, that require close proximate to the body. Current construction of head and c-spine coils is such that the visual field as needed for viewing a fixed positioned fiber taper is either obscured or completely blocked if the fiber taper is utilized.

Another prior art device is disclosed in U.S. Pat. No. 5,414,459 directed to a pair of glasses worn by the patient. The glasses receive the video picture by fiberoptic guide.

In both theses devices the installation is permanent with a fiberoptic connection between the shielded MRI room and a remote location housing the operating elements of the system. The connection requires the shielding which surrounds the MRI room to be breeched and that penetration must be adequately protected.

Yet another known device utilized in combination with an MRI apparatus for purposes of patient comfort is a mirror optical system mounted on a spectacle frame and secured to the patient's head. In operation, the patient lies on the scanner table wearing the optical mirror system so that the, patient can view over their head so as to watch a television set placed outside of the bore. The mirror mounted spectacles allow use of a head coil, c-spine, or other skin surface mounted coils. A problem with the spectacle mounted mirror system is that it blocks forward viewing and does not accommodate image tilting should the patient turn their head.

Thus, what is lacking in the art is a device that provides the clarity of reproduction only possible by the close proximity of the patient to the viewing screen. The close proximity allows a small image to provide a large field of view.

Also, lacking in the prior art is an orientation of the screen, in relation to the patient, that permits unobstructed viewing of the entire screen.

In using the prior art viewing devices with the screen outside the bore of the apparatus, the patient's field of view inherently includes exterior surroundings which can include distractions. Therefore, the prior art lacks a structure which can eliminate the appearance of unintended stimuli.

SUMMARY OF THE INVENTION

The present invention satisfies this need through the provision of a magnetically inert and RF shielded LCD projector located closely adjacent the MRI bore. The projector is used with a screen that is located inside the MRI bore near the patient's head. The short distance between the projector and screen permits a very narrow beam to be passed above the patient and below the top of the MRI bore while providing an unobstructed picture for viewing. The magnetically inert projector is fed the video signal by fiberoptic cable from a source which may be placed within the room but outside the magnetic field of the MRI. In this manner, the entire apparatus is made portable.

The screen is movably placed inside the bore of the MRI in a vertical orientation between the top of the bore and the patient. The screen is of translucent material which allows projection from either end of the MRI bore.

The supine patient views the screen through an adjustable prism or other mechanism having reflecting elements that can change the line of sight through 90 degrees. The viewing device is located in his near field of vision.

The relative closeness of the screen to the patient's eyes and the projector allows full picture viewing for patients of differing sizes.

Thus, a primary objective of the instant invention is to provide a video within an MRI apparatus to view a visual image that is superimposed on a translucent surface allowing the viewing of the displayed image as well as the immediate surroundings.

Yet another object of the instant invention is to provide an LCD projector that is magnetically inert, RF shielded and is passively cooled without a motorized fan.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
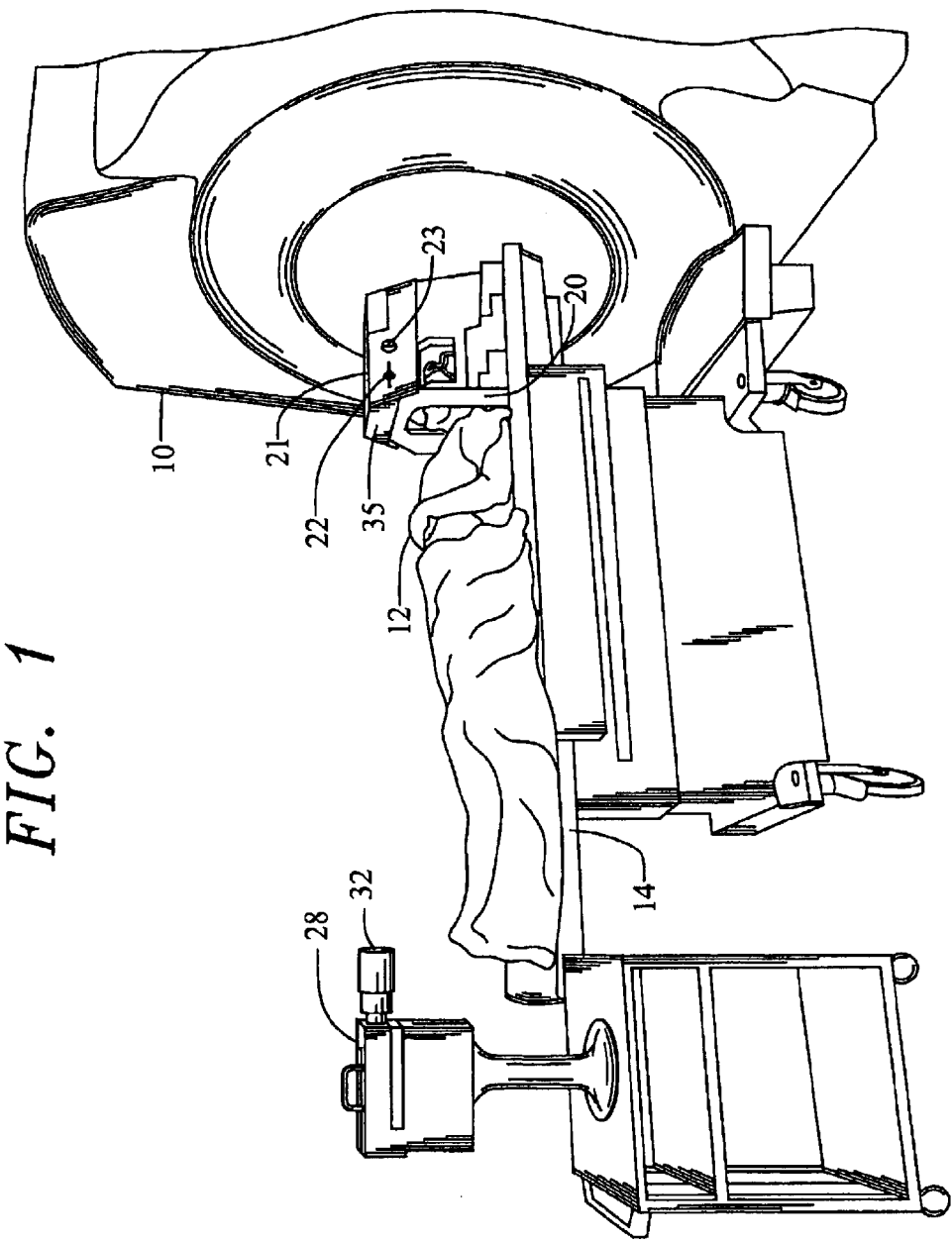
FIG. 1 is a perspective view of an MRI apparatus with the instant invention placed over the patient laying on the MRI table.

Now referring to FIG. 1, a pictorial view of a conventional magnetic resonance image (MRI) apparatus 10 depicts a patient 12 lying on a scanner table 14 and prepared for diagnostic imaging. Imaging is performed by the use of the magnetic coils at the center of the bore to produce a magnetic gradient that can be interpreted by a processing computer. The MRI apparatus 10 is placed within a shielded room 18 that is typically separated from a control room 19 to allow an operator to monitor the patient 12 without disrupting the imaging process. The control room and viewing glass between the control room and MRI shields both the scanning device from external interference and the operator from excess EMF's. As shown in FIG. 1, the patient's head is located within an open tubular coil 20. The screen housing 21 sits on top of the device. The housing 21 has a slide control 22 for adjusting the horizontal position of the screen 35 in relation to the patient's eyes. The rotary control 23 adjusts the angle of the prism or mirror 34 to direct the line of sight toward the screen.

The display system controls stimuli to a patient 12 while lying in a horizontal position on the scanner table 14 by use of a video interface 24 which is coupled to the projector 28. The video interface receives power through AC line 60. The video interface also powers the projector through a DC line 37. The video interface 24 is operatively connected to a VGA source computer 26 and a VGA monitor 36 for selective use during the procedure. The video interface, VGA computer and VGA monitor are located outside the shielded room housing the MRI apparatus or otherwise shielded to prevent interfering radio frequency produced during the scan or by the video device. However, the only penetration of the shielding is the fiberoptic cable 30 and a DC power connection 37. The video interface 24 can be used to control the visual image delivered to the patient providing color correction, buffered video output for VGA monitor, and provide messages to the patient for constant communication. The video interface 24 is coupled to a colored liquid crystal display LCD projector 28 by fiberoptic cable 30. The projector 28 is shown located at the end of the MRI apparatus 10. The LCD projector is coupled to an optical lens assembly 32 which projects the video to screen 35 by a narrow beam.

Figure 2:
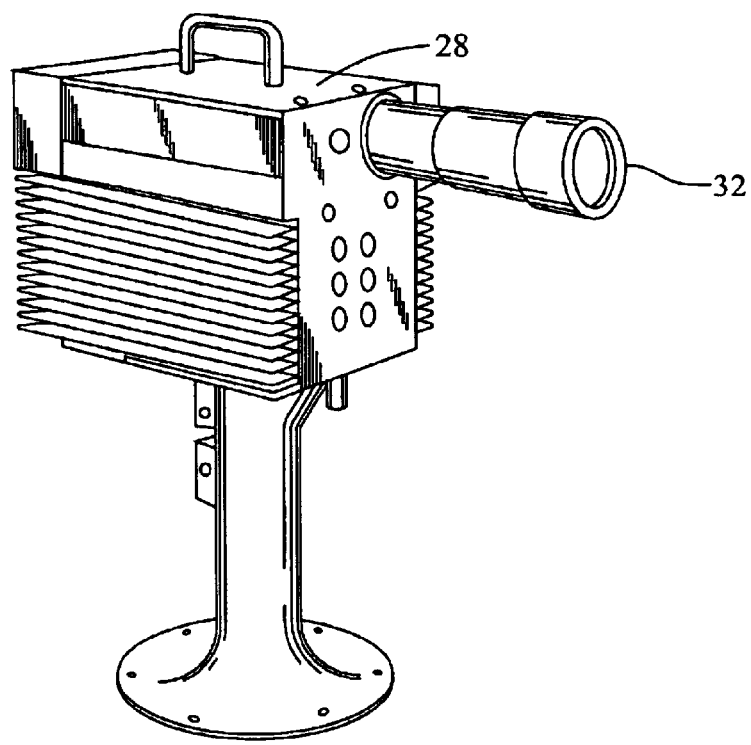
FIG. 2 is a perspective of the projector of this invention.
Figure 4:
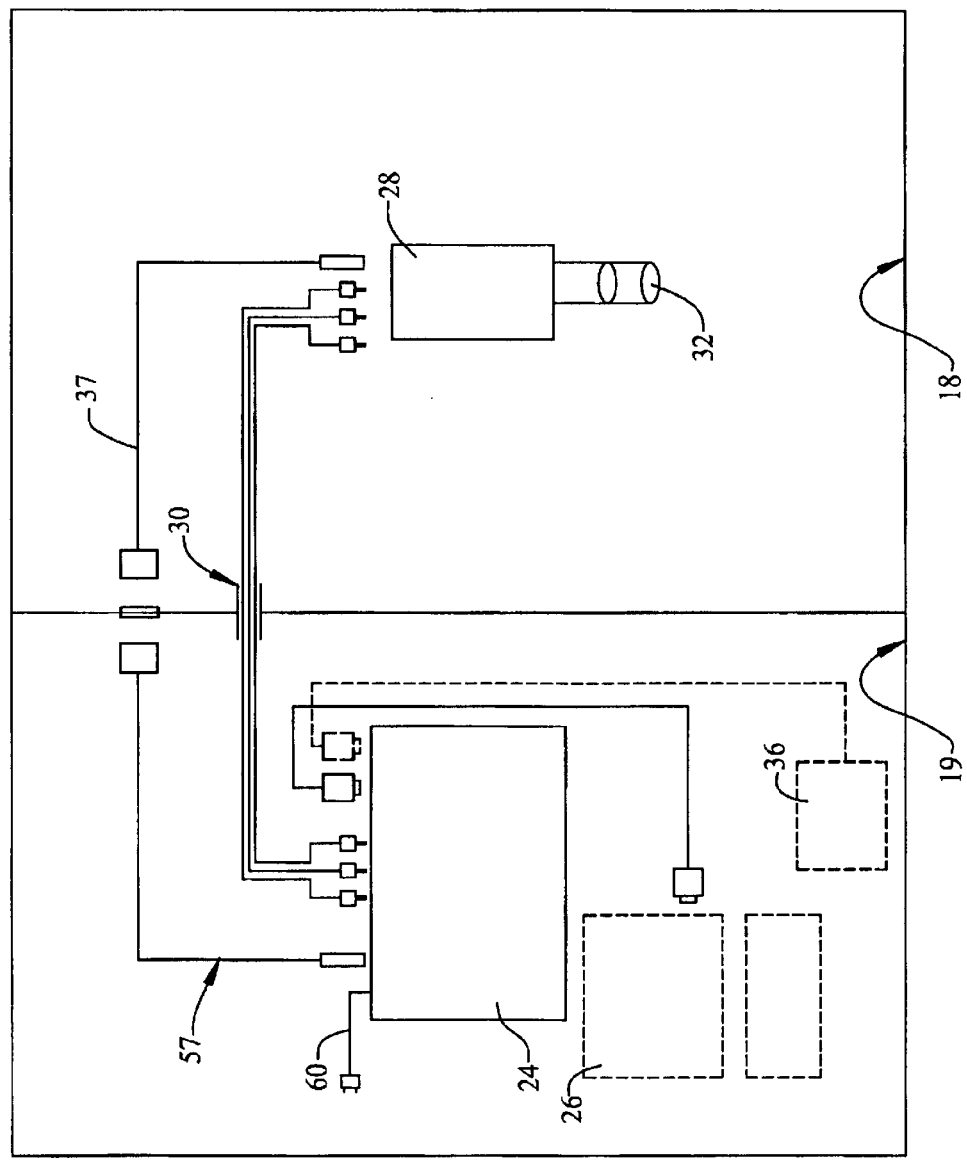
FIG. 4 is a schematic of the system.
Figure 5:
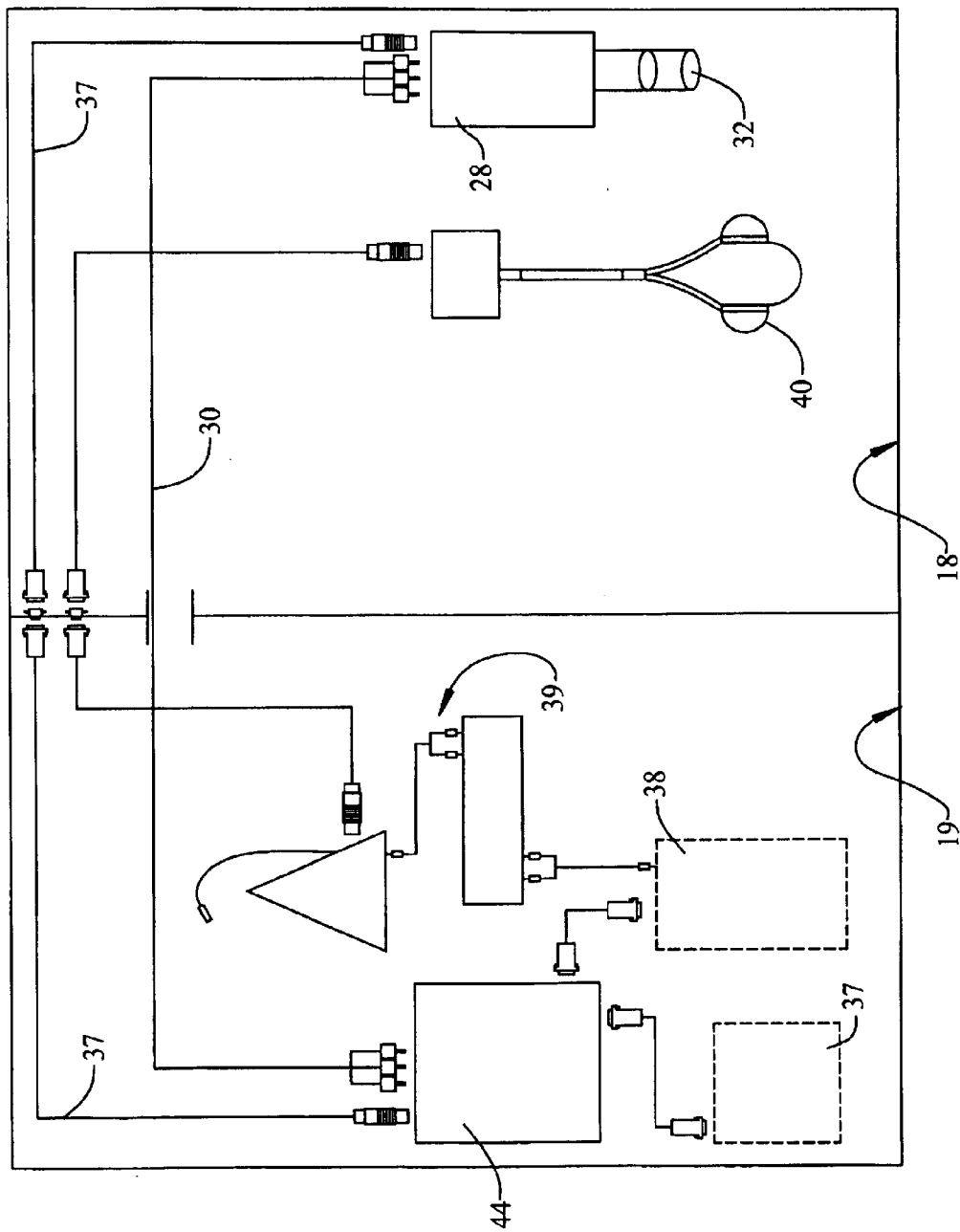
FIG. 5 is a schematice of another modification of the invention.

FIGS. 4 and 5 set forth simplified block diagrams of the system wherein the video interface 24 is coupled to the VGA source computer 26 and the VGA monitor 36. The video interface 24 is further coupled to a colored liquid crystal display LCD projector 28 by fiberoptic cable 30. The projector lens 32 directs the picture to the translucent screen 35 located in the bore of the MRI. The patient views the picture from a supine position through prism 34. In FIG. 2, the prism 34 or other viewing device, such as a periscope with reflective elements, is located approximately over the eyes of the patient. The projector 28 is located at either end of the MRI bore and the translucent screen 35 is located near the top of the bore in the area between the patient's chin and waist. In some MRI apparatus the bore is smaller than shown in FIG. 1, in these systems the viewing screen:may be adapted to be supported by or on the patient's head.

FIG. 5 sets forth an alternative embodiment of the instant invention wherein the video interface 44 is coupled to a remote monitor 37 and a stimulus computer 38. The stimulus monitor 38 is also connected to an audio system 39 which has a head set 40 for the patient. The audio system 39 provides direct communication between the patient and the operator. In particular, the external audio communicator can attach to a video camera that allows the patient to see and communicate directly with the operator. In addition, the communication device provides a means for controlling the visual stimuli that reaches each eye of the patient. Thus, the system can be used to stimulate the patient for a specialized test. The video interface is coupled to the projector 48 by fiberoptic cable 50. The LCD projector 48 can be placed at the either end of the MRI bore and project the picture on the translucent screen 35 located above the patient's chest area.

Figure 3:
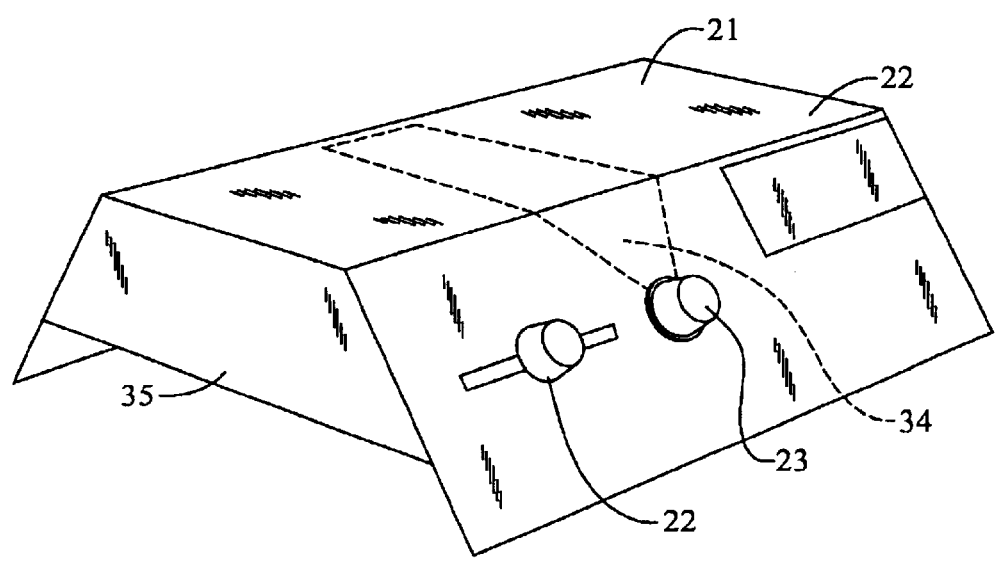
FIG. 3 is a perspective of the screen housing.

The apparatus shown in FIGS. 2 and 3 may be permanently affixed to an MRI or the apparatus may be temporarily mounted in the operative position. When temporarily mounted, the entire system is portable. The system does not require any disturbance of the continuity of shielding of the MRI room.

The specific connection of components of this viewing apparatus and the MRI have not been shown because it is considered to be within the ability of one having ordinary skill in the art to fabricate and attach the mounting elements.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A method of alleviating symptoms of claustrophobia in a patient laying within a bore of a Magnetic Resonance Imaging (MRI) apparatus positioned within a shielded area comprising the steps of:
   a) providing a liquid crystal display (LCD) video image projector positioned inside the shielded area adjacent the bore of the apparatus, said projector constructed to be magnetically inert and RF shielded and including an optical lens to project said images, a translucent screen for displaying said projected images and a viewing device for altering a line of sight from said screen,
   b) providing a source of video images positioned outside the shielded area;
   c) coupling said projector and said source of video images using a fiberoptic cable wherein said fiberoptic cable penetrates the shielded area;
   d) placing said screen in the bore of the apparatus,
   e) projecting said images on said screen,
   f) placing said viewing device between said patient and said screen to alter the line of sight between said patient and said screen whereby said patient may view video images within the bore of said MRI.

2. The method of claim 1 including the step wherein g) said patient looks into said viewing device and said line of sight is altered approximately 90 degrees to view said video images on said screen.

3. The method of claim 1 including the steps wherein
   g) a video stimulus is projected on said screen and
   h) the patient's reaction is recorded.

4. The method of claim 2 including the steps wherein said patient g) adjusts the horizontal position of said screen and h) angularly rotates said line of sight.

5. A video viewing system for use in an MRI apparatus positioned in a shielded area having a bore for housing a patient, said system comprising a source of video images connected to a liquid crystal display (LCD) video projector by a fiberoptic cable wherein said fiberoptic cable penetrates the shielded area, said projector adapted to be placed within a magnetic field of the apparatus and constructed to be magnetically inert and RF shielded, a screen adapted to be placed in the bore of the apparatus for receiving projected video images and a viewing device containing reflective elements adapted for placement in the bore and optically associated with said screen.

6. A video system of claim 5 wherein said LCD projector is passively cooled.

7. A video system of claim 5 wherein said screen is translucent.

8. A video system of claim 5 wherein said viewing device is adapted for mounting on the patient's head.

9. A video system for providing video images in an MRI apparatus positioned in a shielded area, the apparatus having a bore for receiving a patient, comprising a video screen mounted in the bore; a periscopic viewing device mounted in the bore in line of sight with said screen, said periscopic viewing device having reflective elements altering said line of sight approximately 90 degrees; and a magnetically inert and RF shielded liquid crystal display (LCD) video projector located within a magnetic field of the MRI apparatus in a line of sight with said screen, wherein said LCD projector is connected to a source of video images positioned outside the shielded area by a fiberoptic cable wherein said fiberoptic cable penetrates the shielded area.

10. A video system of claim 9 wherein said screen is translucent.

11. A video system of claim 9 wherein said screen and said viewing are mounted in a housing, said housing having a means for adjusting the horizontal position of said screen in said housing, said housing having a means for angularly adjusting the line of sight.

* * * * *